(12) United States Patent
Shapiro et al.

(10) Patent No.: US 6,372,791 B1
(45) Date of Patent: Apr. 16, 2002

(54) METHOD OF PROMOTING SKIN CELL METABOLISM

(75) Inventors: Stanley S. Shapiro, Livingston; Katharine M. Martin, Ringoes, both of NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/606,556

(22) Filed: Jun. 29, 2000

(51) Int. Cl.[7] .......................... A61K 31/19; A01N 37/00
(52) U.S. Cl. ...................... 514/557; 514/561; 424/401; 424/78.02
(58) Field of Search .............................. 424/401, 78.02; 514/561, 557, 844–846

(56) References Cited

U.S. PATENT DOCUMENTS

| | | |
|---|---|---|
| 3,755,560 A | 8/1973 | Dickert et al. |
| 4,254,105 A | 3/1981 | Fukuda |
| 4,320,145 A | 3/1982 | Cavazza |
| 4,421,769 A | 12/1983 | Dixon et al. |
| 4,960,764 A | 10/1990 | Figueroa, Jr. et al. |
| 4,961,927 A | 10/1990 | Kogure |
| 5,106,624 A | 4/1992 | Panna |
| 5,376,379 A | 12/1994 | Fabre et al. |
| 5,531,993 A | 7/1996 | Griat |
| 5,536,751 A | 7/1996 | Bunger |
| 5,578,312 A | 11/1996 | Parrinello |
| 5,627,212 A | 5/1997 | Cavazza et al. |
| 5,637,305 A | 6/1997 | Cavazza et al. |
| 5,641,814 A | 6/1997 | Martin |
| 5,690,946 A | 11/1997 | Koulbanis et al. |
| 5,756,107 A | 5/1998 | Hahn et al. |
| 5,759,610 A | 6/1998 | Nishimoto et al. |
| 5,821,237 A | 10/1998 | Bissett et al. |
| 5,928,657 A | 7/1999 | Simon |
| 5,932,234 A * | 8/1999 | Simon et al. ............... 424/401 |
| 5,935,636 A | 8/1999 | Nishimoto et al. |
| 5,951,990 A | 9/1999 | Ptchelintsev |
| 5,997,885 A | 12/1999 | Koulbanis et al. |
| 6,033,684 A | 3/2000 | Norcia |
| 6,106,846 A | 8/2000 | Breton et al. |

FOREIGN PATENT DOCUMENTS

| | | |
|---|---|---|
| EP | 0 413 528 A1 | 2/1991 |
| EP | 0 573 465 B1 | 12/1993 |
| EP | 0 600 730 B1 | 6/1994 |
| EP | 0273202 B1 | 6/1995 |
| EP | 0 711 543 A1 | 5/1996 |
| EP | 0 717 984 A2 | 6/1996 |
| EP | 0 868 916 A2 | 10/1998 |
| EP | 0 974 342 A1 | 1/2000 |
| EP | 0 983 727 A2 | 3/2000 |
| EP | 0 998 914 A1 | 5/2000 |
| FR | 1248192 | 1/1960 |
| FR | 3574 M | 5/1964 |
| FR | 2619007 | 2/1989 |
| FR | 2627385 | 8/1989 |
| GB | 0559502 | 3/1996 |
| GB | 0699432 | 1/1997 |
| GB | 0773012 | 11/1997 |
| GB | 0846462 | 12/1999 |
| JP | 51148042 A * | 12/1976 |
| WO | WO 84/04885 A1 | 12/1984 |
| WO | WO 89/06958 A1 | 8/1989 |
| WO | WO 95/03028 A1 | 2/1995 |
| WO | WO 95/04537 A1 | 2/1995 |
| WO | WO 95/13793 A1 | 5/1995 |
| WO | WO 95/27501 A1 | 10/1995 |
| WO | WO 96/11572 A1 | 4/1996 |
| WO | WO 97/15282 A1 | 5/1997 |
| WO | 99/07388 A1 | 7/1998 |
| WO | 99/08681 A1 | 8/1998 |
| WO | WO 98/51277 A1 | 11/1998 |
| WO | WO 00/04870 A2 | 2/2000 |

OTHER PUBLICATIONS

Abstract of JP 51148042 publication date Dec. 17, 1976.
EPO Search Report dated Jul. 25, 2001 for Application No. 00 307 058.8–2114.
Evian Moisture Cream package and translation.
Evian Moisture Lotion Gentle product bottle and translation.
Evian Oil Free Skin Lotion product bottle and translation.
Evian Washing Cream product tube and translation.
Evian Moisture Cream product jar and translation.
Evian packaging insert for Evian Washing Cream, Skin Lotion and Moisture Lotion.
Medical Guide to the Mineral Waters of France and its Wintering Stations, A. Vintras, M.D., 1883, J&A Churchill, London, pp. 261–263.
Balsom, P., Soderlund, K. and Ekbom, B., Creatine in Humans with Special Reference t Creatine Supplementation, Sports Med. 1994, 268–280, 18 (4).
Bremer, J., Carniture–Metabolism and Functions, Physiological Reviews, 1983, 1420–1480, vol. 63 No. 4.
Stanko, R., Tietze, D. and Arch, Body Compositin, energy utilization, and nitrogen metabolism with a 4.25–MJ/d low–energy diet supplemented, American Journal Clinical Nutr. 1992, 630–635, vol. 56 (4).
Evian "Le brumisatuer©", S.A. des Eaux Minerales d'Evian , excerpt taken from WATER . . . IT'S LIFE., Evian publication dated 5/97.
Wenninger, J.A. et al., International Cosmetic Ingredient Dictionary and Handbook, vol. 2, Seventh Ed. (1997), pp. 1612–1613, 1626, 1654–1661, 1673–1686, 1693–1697.

(List continued on next page.)

Primary Examiner—Jose ' G. Dees
Assistant Examiner—Konata George
(74) Attorney, Agent, or Firm—William E. McGowan

(57) ABSTRACT

The present invention relates to a method of promoting metabolism, energy production, and the uptake and utilization of oxygen in the skin comprising topically administering a promoting amount of (i) carnitine or a therapeutically acceptable salt or ester thereof and (ii) pyruvic acid or a therapeutically acceptable salt or ester thereof.

28 Claims, No Drawings

OTHER PUBLICATIONS

Balsam, M.S. and Sagarin, E., Cosmetics Science And Technology, vol. 1, Second Ed. John Wiley & Sons, Inc. (1972), pp. 72–73 and 443–465.

McCutcheon's Emulsifiers & Detergents, pp. 317–324 (1986).

Evian Le Brumisateur Eau Minerale Natures, product information (9 sheets) (dated prior to Jun. 29, 1999).

U.S. application No. 09/606,490, Johnson & Johnson Consumer Companies, Inc., pending.

U.S. application No. 09/607,118, Johnson & Johnson Consumer Companies, Inc., pending.

U.S. application No. 09/606,889, Johnson & Johnson Consumer Companies, Inc., pending.

U.S. application No. 09/606,557, Johnson & Johnson Consumer Companies, Inc., pending.

U.S. application No. 09/606,491, Johnson & Johnson Consumer Companies, Inc., pending.

EPO Search Report Dated Nov. 17, 2000 for Patent application No. 00307058.

* cited by examiner

METHOD OF PROMOTING SKIN CELL METABOLISM

FIELD OF THE INVENTION

The present invention relates to a method of promoting skin cell metabolism.

BACKGROUND OF THE INVENTION

In order to survive and work properly, eukaryotic cells require energy. This energy comes mostly from the diet. In fact, foodstuffs get successively digested and metabolized to simple molecular entities that the individual cells, using their mitochondria, can convert into energy. However, the mitochondrial membranes are only permeable to certain molecules. For this reason, carbohydrates and certain amino acids have to be broken down in the cytosol into pyruvate. In contrast, fatty acids can be absorbed by the mitochondria with the help of a specific carrier, L-carnitine.

Once these nutrients are inside the mitochondria, they are further metabolized to a 2-carbon molecule, acetyl-coenzyme A (acetyl CoA) that fuels the tricarboxylic acid cycle also known as Krebs cycle. This cycle generates carbon dioxide ($CO_2$) and electron-transporters NADH and FADH2 that feed the electron transport chain or respiratory chain reducing oxygen ($O_2$) into water ($H_2O$) and generating a proton gradient. This proton gradient creates a natural flow back into the mitochondrial matrix through a protein complex that produces ATP, the principle cellular energy store. For example, ATP is directly used in biochemical synthesis, signal transduction, cell movement, cellular division, and ion pumping.

The main oxygen consumer in the skin are the mitochondria, which are responsible for skin cell energy metabolism. Oxygen consumption in skin cells (e.g., uptake into and/or utilization by the cells) impacts on skin health, e.g., skin firmness and elasticity, skin tone/texture, and skin barrier function.

SUMMARY OF THE INVENTION

The invention features a method of promoting skin cell metabolism, e.g., promoting energy production or the uptake of oxygen into and/or the utilization of oxygen ($O_2$) in the skin, comprising topically administering a promoting amount of (i) carnitine or a therapeutically acceptable salt or ester thereof and (ii) pyruvic acid or a therapeutically acceptable salt or ester thereof.

What is meant by promoting energy production is increasing metabolic activity in the skin (e.g., the production of ATP in the skin cells or the increase of mitochondrial activity in the skin cell). What is meant by promoting the uptake of oxygen is either (i) increasing the amount of oxygen stored in the skin cell or (ii) increasing the rate by which oxygen is taken in by the skin cell. What is meant by promoting the utilization of oxygen is either (i) increasing the amount of oxygen utilized, e.g., converted to $CO_2$ or other compounds, in the skin cell or (ii) increasing the rate by which oxygen is utilized by the skin cell. In one embodiment, the increase in an amount or rate is at least about 5% such as at least about 20%.

In one embodiment, the method further comprises topically administering mineral water having a mineralization of at least about 200 mg/L, e.g., wherein the mineral water comprises at least about 10 mg/L of calcium and about 5 mg/L of magnesium.

The promotion of oxygen consumption in the skin (e.g., uptake into and/or utilization by the cells) provides healthier skin, e.g., enhances skin firmness and elasticity, evens skin tone/texture, makes skin more radient, enhances skin glow, and enhances skin barrier function.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to promoting skin cell metabolism. In one embodiment, the method further comprises topically administering mineral water. What is meant by mineral water is water having mineralization (i.e., the sum of the concentrations of anions and cations present in the water) of at least about 200 mg/L (e.g., at least about 300 mg/L such from about 400 mg/L to about 1000 mg/L). Examples of such anions and cations include, but are not limited to, calcium, magnesium, bicarbonates, sulfates, potassium, sodium, chlorides, nitrates, phosphates, lithium, manganese, sulfites, fluoride, and iodide. In one embodiment, the mineral water has at least about 5 mg/L, e.g., at least about 10 mg/L, of magnesium and at least about 10 mg/L, e.g., at least about 20 mg/L, of calcium.

The mineral water may be a naturally mineralized water, e.g., a mineral water suitable for consumption, or a thermal spring water, which is often not consumable. Examples of mineral water include, but are not limited to, eau d'Evian (Evian Eau Minerale Naturelle or Evian® Natural Spring Water referred herein as Evian® Mineral Water), eau Volvic, and eaux de Vittel (e.g., Grande Spring or Hepar Spring).

Examples of thermal spring waters include eau de la Bourboule, eau d'Enghien-les-bains, eau d'Allevard-les-bains, eau de Digne, eau des Maizieres, eau de Nyrac-les-bains, eau de Lons le Saunier, Eaux Bonnes, eau de Rochefort, eau de Saint Christau, eau des Fumades, eau de Tereau de Vittel, eaux du bassin de Vichy, eau d'Uriage, eau d'Avene, and eau de la Roche Posay.

In one embodiment, the mineral water comprises (a) from about 30 mg/L to about 150 mg/L of calcium; (b) from about 10 mg/L to about 50 mg/L of magnesium; (c) from about 150 mg/L to about 700 mg/L of bicarbonates; (d) from about 0.1 mg/L to about 5 mg/L of potassium; (e) from about 1 to about 20 mg/L of sulfates; (f) from about 1 to about 10 mg/L of sodium; (g) from about 1 mg/L to about 10 mg/L of chlorides; and (h) from about 1 mg/L to about 10 mg/L of nitrates.

In one embodiment, the mineral water is Evian® Mineral Water that comprises: (a) about 78 mg/L of calcium, (b) about 24 mg/L of magnesium, (c) about 357 mg/L of bicarbonates; (d) about 1 mg/L of potassium; (e) about 10 mg/L of sulfates; (f) about 5 mg/L of sodium, (g) about 4 mg/L of chlorides from about 1 to about 4 mg/L nitrates.

The methods of the present invention comprise the use of carnitine and pyruvic acid, or a cosmetically acceptable salt or ester thereof. What is meant by cosmetically acceptable salt or ester is one that does not eliminate the therapeutic benefit of the compound (e.g., the promotion/enhancement of cell metabolism). Examples of cosmetically acceptable salts include, but are not limited to, those with cosmetically acceptable organic acids (e.g., acetic, lactic, maleic, citric, malic, ascorbic, succinic, benzoic, methesulfonic, toluenesulfonic, or pamoic acid), as well as polymeric acids (e.g., tannic or carboxymethyl cellulose) and salts with inorganic acids such as a hydrohalic acid (e.g., hydrochloric acid, sulfuric acid, or phosphoric acid). Examples of cosmetically acceptable esters include, but are not limited to, C2–C6 alkyl esters such as methyl esters and ethyl esters. Examples of such compounds include, but are not limited to, D-carnitine, L-carnitine, L-carnitine hydrochloride, sodium pyruvate, and pyruvic acid methyl ester. As used herein, if the stereochemistry of the compound is not indicated, then the compound includes all stereoisomers, if any.

In one embodiment, the method of the present invention further comprises topically administering (e.g., in a composition) a nutrient to the skin cells. What is meant by a nutrient is an organic substance occurring in foods that is not synthesized by the body and is necessary in trace amounts for the normal metabolic functioning of the body, such as vitamins, essential amino acids, and essential fatty acids.

Examples of such vitamins include, but are not limited to, vitamin A, a vitamin B (e.g., vitamin B1, vitamin B2, vitamin B6, or vitamin B12), vitamin C, and a vitamin E (e.g., a tocopherol or tocotrienol), and a cosmetically acceptable salts and esters thereof, such a retinyl palmitate, retinyl acetate, tocopherol succinate, and tocopherol acetate.

Examples of such essential amino acids include, but are not limited to, arginine, histidine, isoleucine, leucine, lysine, methionine, phenylalanine, threonine, tryptophan, and valine.

Examples of essential fatty acids include, but are not limited to, linoleate and linolenate.

In one embodiment, the method of the present invention further comprises topically administering (e.g., in a composition) an emollient and/or a humectant to the skin cells. What is meant by an emollient is a compound that helps to maintain the soft, smooth, and pliable appearance of the skin (e.g., by remaining on the skin surface or in the stratum corneum to act as a lubricant). Examples of emollients can be found on pages 1657–1661 of the International Cosmetic Ingredient Dictionary and Handbook, eds. Wenninger and McEwen, pp. 1612–13, 1626, and 1654–55 (The Cosmetic, Toiletry, and Fragrance Assoc., Washington, D.C., 7$^{th}$ Edition, 1997) (hereinafter "ICI Handbook"), and include, but are not limited to, hexyldecyl stearate and plant, nut, and vegetable oils such as macadamia nut oil, rice bran oil, grape seed oil, palm oil, primrose oil, hydrogenated peanut oil, olive oil, and avocado oil.

What is meant by a humectant is a compound intended to increase the water content of the top layers of skin (e.g., hygroscopic compounds. Examples of humectants can be found on pages 1661–1662 of the ICI Handbook and include, but are not limited to, glycerin or trehalose (e.g., α,α- trehalose, β,β-trehalose, α,β-trehalose) or a salt or ester thereof (e.g., trehalose 6-phosphate).

What is meant by a promoting amount is an amount capable of promoting the desired effect (e.g., promoting metabolism, energy production and the uptake/utilization of oxygen by skin cells). The amount of carnitine or a cosmetically acceptable salt or ester thereof, pyruvic acid or a cosmetically acceptable salt or ester thereof, nutrient, emollient, or humectant in the composition varies (e.g., depending on the intended use or the form of the composition) being administered and will typically be present in the composition in an amount from about 0.001% to about 20% by weight of the composition, e.g., from about 0.01% to about 10% such as from about 0.01% to about 5% of such emollient or humectant and from about 0.001% to about 10% by weight of the composition, e.g., from about 0.01% to about 5% such as from about 0.01% to about 1% of such carnitine or a cosmetically acceptable salt or ester thereof and pyruvic acid or a cosmetically acceptable salt or ester thereof.

In one embodiment, the method further comprises administering (e.g., in a composition) another cosmetically active agent. What is meant by a "cosmetically active agent" is a compound that has a cosmetic or therapeutic effect on the skin, e.g., agents to treat wrinkles, acne, or to lighten the skin. In one embodiment, the agent is selected from, but not limited to, the group consisting of hydroxy acids, benzoyl peroxide, sulfur resorcinol, ascorbic acid, D-panthenol, hydroquinone, sunscreen agents, anti-inflammatory agents, skin lightening agents, antimicrobial and antifungal agents, estrogens, 2-dimethylaminoethanol, lipoic acid, amino acids such a proline and tyrosine, lactobionic acid, acetyl-coenzyme A, niacin, riboflavin, thiamin, ribose, electron transporters such as NADH and FADH2, botanical extracts such as aloe vera and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of hydroxy acids include, but are not limited to (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

The method of the present invention can be practiced by topically administering to a mammal, e.g., by the direct laying on or spreading on the skin of a human, a safe and effective amount of carnitine or a cosmetically acceptable salt or ester thereof and a safe and effective amount of pyruvic acid or a cosmetically acceptable salt or ester thereof in a composition. The compositions (e.g., cosmetic compositions) useful in the subject invention involve formulations suitable for topical application to mammalian skin, the formulation comprising (i) a safe and effective amount of carnitine or a cosmetically acceptable salt or ester thereof, (ii) a safe and effective amount of pyruvic acid or a cosmetically acceptable salt or ester thereof, (iv) optionally, mineral water (e.g., in which the compounds of (i) an (ii) are dissolved or suspended, (v) optionally, a nutrient, an emollient, humectant (e.g., trehalose), or other cosmetically active agent(s), and (vi) optionally, a cosmetically-acceptable topical carrier. The term "cosmetically-acceptable topical carrier" refers to a carrier for topical use that is capable of having the components of the present invention (e.g., carnitine and pyruvic acid) dispersed or dissolved therein, and possessing acceptable safety properties.

The topical compositions useful in the present invention may be used for a variety of cosmetic uses, including, but not limited to, treating, cleansing, beautifying, or covering the skin or hair of a human. The compositions, thus, may be made into a wide variety of product types. These include, but are not limited to lotions, creams, gels, sticks, sprays, ointments, pastes, mousses, shampoos, cosmetics, and dermal patches. Products include, but are not limited to, lip balms, moisturizing and sunscreen lotions/creams, skin cleansing compositions (e.g., facial scrubs), and body mists. These products may comprise several types of carrier systems including, but not limited to single phase solutions (e.g., aqueous or oil based solutions), emulsions, and gels. In one embodiment, mineral water is used to form the cosmetically acceptable topical carrier.

The topical compositions useful in the present invention formulated as solutions typically include a cosmetically acceptable water, mineral water, and/or organic carriers (e.g., from about 80% to about 99.99%, by weight of the compositions such as from about 90% to about 99%, by weight of the composition, of an acceptable aqueous or organic solvent). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, butanediol, and mixtures thereof.

If the topical solution useful in the present invention are formulated as an aerosol and applied to the skin as a spray-on, a propellant is added to a solution composition. Examples of propellants useful herein include, but are not limited to, chlorinated, fluorinated, and chloro-fluorinated lower molecular weight hydrocarbons. Other propellants useful herein can be found in Sagafin, Cosmetics Science and Technology, 2nd Edition, Vol. 2, pp. 443–65 (1972) (hereinafter "Sagafin") and the ICI Handbook pp. 1655.

A lotion can be made from a solution carrier system. Lotions typically comprise from about 1% to about 20% by weight of the composition (e.g., from about 5% to about 10%) of an emollient(s) and from about 50% to about 90% by weight of the composition (e.g., from about 60% to about 80%) of water.

Another type of product that may be formulated from a solution carrier system is a cream. A cream typically comprises from about 5% to about 50% by weight of the composition (e.g., from about 10% to about 20%) of an emollient(s) and from about 45% to about 85% by weight of the composition (e.g., from about 50% to about 75%) of water.

Yet another type of product that may be formulated from a solution carrier system is an ointment. An ointment may comprise a simple base of animal or vegetable oils or semi-solid hydrocarbons. Ointments may also comprise absorption ointment bases that absorb water to form emulsions. Ointment carriers may also be water-soluble. An ointment may comprise from about 1% to about 20% by weight of the composition of an emollient(s) plus from about 0.1% to about 2% by weight of the composition of a thickening agent(s). A more complete disclosure of thickening agents or viscosity increasing agents useful herein can be found in Sagafin pp. 72–73 and the ICI Handbook pp. 1693–97.

If the carrier is formulated as an emulsion (e.g., an oil-in-water, silicone-in-water, water-in-oil, or water-in-silicone emulsion), from about 1% to about 10% by weight of the composition (e.g., from about 2% to about 5%) of the carrier system may comprise an emulsifier(s). Emulsifiers may be nonionic, anionic, cationic, or zwitterionic. Suitable emulsifiers are disclosed in, for example, U.S. Pat. No. 3,755,560, U.S. Pat. No. 4,421,769, McCutcheon's Detergents and Emulsifiers, North American Edition, pp. 317–24 (1986), and the ICI Handbook, pp.1673–86.

Lotions and creams can also be formulated as emulsions. Typically, such emulsions may comprise from 0.5% to about 5% by weight of the composition of an emulsifier(s). Creams may typically comprise from about 1% to about 20% by weight of the composition (e.g., from about 5% to about 10%) of an emollient(s); from about 20% to about 80% by weight of the composition (e.g., from about 30% to about 70%) of water; and from about 1% to about 10% by weight of the composition (e.g., from about 2% to about 5%) of an emulsifier(s).

Two phase emulsion skin care preparations, such as lotions and creams, of the oil-in-water type and water-in-oil type are well-known in the cosmetic art and are useful in the subject invention. Triphase emulsion compositions, such as the water-in-oil-in-water type, as disclosed in U.S. Pat. No. 4,254,105, are also useful in the subject invention. In general, such triphase emulsions contain water, emollients, and emulsifiers as essential ingredients. Triple emulsion carrier systems comprising an oil-in-water-in-silicone fluid emulsion composition, as disclosed in U.S. Pat. No. 4,960,764, may also be useful in the subject invention.

If the topical compositions useful in the subject invention are formulated as a gel or a cosmetic stick, such compositions can be formulated by the addition of a suitable amount of a thickening agent, as disclosed supra, to a cream or lotion formulation.

The methods of the present invention may also comprise administering a composition containing one or more of the following: antioxidants (e.g., ascorbic acid, tocopherols, polyphenols, tocotrienols,BHA, and BHT), chelating agents (e.g., EDTA), and preservatives (e.g., parabens). Examples of suitable antioxidants, preservatives, and chelating agents are listed in pp. 1612–13, 1626, and 1654–55 of the ICI Handbook. In addition, the topical compositions useful herein can contain conventional cosmetic adjuvants, such as dyes, opacifiers (e.g., titanium dioxide), pigments, and fragrances.

The compositions and cosmetic formulations for use in the methods of the present invention may be prepared using methodology that is well known by an artisan of ordinary skill. The following is a description of the testing and manufacturing of cosmetic compositions of the present invention.

EXAMPLE 1

Mineral Water Containing Carnitine, Trehalose, and Sodium Pyruvate

A composition containing Evian® Mineral Water (Evian, France), carnitine, sodium pyruvate, and trehalose was manufactured using the ingredients listed in Table I.

TABLE I

| INGREDIENTS | % Weight |
|---|---|
| L-Carnitine | 1 |
| Sodium Pyruvate | 1 |
| Trehalose | 1 |
| D-Panthenol (75%)/Water (25%) | 1.3 |

TABLE I-continued

| INGREDIENTS | % Weight |
| --- | --- |
| Magnesium Ascorbyl Phosphate | 1 |
| L-Proline | 1 |
| Mineral Water | 72.7 |
| Pentylene Glycol | 20 |
| Phenoxyethanol | 1 |

The mineral water was first heated to 30° C. The other ingredients were then added and dissolved one by one under mixing conditions. The pentylene glycol was obtained from Dragoco Gerberding & Co. (Holzminden, Germany) under the tradename Hydrolite® –5.

EXAMPLE 2

Sunscreen Moisturizer

A sunscreen moisturizing composition containing the composition of Example 1 and the sunscreen octyl methoxycinnamate is manufactured using the ingredients listed in Table II.

TABLE II

| INGREDIENTS | % Weight |
| --- | --- |
| Water Phase Ingredients | |
| Mineral Water | q.s. 100 |
| Disodium EDTA | 0.1 |
| Glycerin | 3 |
| Butylene glycol | 3 |
| Carbomer | 0.25 |
| Acrylate-C10–30 alkyl acrylate crosspolymer | 0.07 |
| Glyceryl polymethacrylate 67%/water 32%/ propylene glycol 1% | 5 |
| Propyl paraben | 0.201 |
| Methyl paraben | 0.35 |
| Phenoxyethanol | 0.584 |
| Oil Phase Ingredients | |
| Cetearyl alcohol | 1 |
| C12–C15 alkyl benzoate | 4 |
| Potassium cetyl phosphate | 1.5 |
| PEG-100 stearate 50%/glyceryl stearate 50% | 0.3 |
| Di-C12–13 alkyl malate | 5 |
| Talc | 1 |
| Phenoxyethanol | 0.365 |
| Propyl paraben | |
| Methyl paraben | |
| Iodopropynyl butylcarbamate 10%/ PEG-4 laurate 90% | 0.1 |
| Octyl methoxycinnamate | 7.5 |
| Butyl methoxydibenzoylmethane | 3 |
| Tocopheryl acetate | 1 |
| Tromethamine Mixture | |
| Mineral Water | 2 |
| Tromethamine | 0.3 |
| Trehalose Mixture | |
| Mineral Water | 2 |
| Trehalose | 0.25 |
| Post Addition Ingredients | |
| Cyclomethicone | 2 |
| Composition of Example 1 | 1 |
| Evening primrose oil | 0.01 |
| Fragrance | 0.3 |

To form the water phase, the mineral water (Evian® Mineral Water, Evian, France) of the Water Phase Ingredients was heated to 85° C. and stirred for about 15 minutes in a first beaker. The disodium EDTA, glycerin, and butylene glycol were then added to the first beaker and stirred for an additional 10 minutes. The first beaker was then cooled to 82° C. Next, the carbomer and the acylate-C10-30 alkyl acrylate crosspolymer were dispersed in the mixture in the first beaker and stirred for about 25 minutes until the mixture gelified. The remaining Water Phase Ingredients were then added to the first beaker and mixed.

To form the oil phase, the Oil Phase Ingredients were added to a second beaker, heated to 85° C. and mixed for 15 minutes. The oil phase mixture in the second beaker was then added to the first beaker under mixing conditions to form an emulsion. The emulsion was then cooled to 25° C. and neutralized with the Tromethamine Mixture. Next, the cyclomethicone was mixed into the emulsion for 15 minutes. Lastly, the Trehalose Mixture, the composition of Example 1, the evening primrose oil, and the fragrance were added to the resulting mixture and mixed until uniform.

EXAMPLE 3

Promotion of Energy Production Using Carnitine and Sodium Pyruvate.

The effects of L-carnitine and sodium pyruvate, in mineral water, on energy production were evaluated in primary normal human dermal fibroblasts (adult). Energy production in the cell is assessed using the REDOX sensitive indicator alamarBlue™ (Alamar Biosciences, Sacramento, Calif.). The native, oxidized form of alamarBlue™ is taken up readily by cells and reduced intracellularly by the mitochondrial electron transport chain, resulting in a shift in its absorbance and fluorescence.

Normal human dermal fibroblasts (NHDF), obtained from Clonetics (Biowhittaker Inc., Walkersville, Md.), were cultured in Clonetics FGM2 medium and grown to confluence in 96-well plates (Costar, Cambridge, Mass.). Culture medium was then replaced with DMEM (Life Technologies, Rockville, Md.) prepared with Evian® mineral water. After 72 hours cells were treated with 10 mM L-carnitine (Biosint USA, Larchmont, N.Y.), 10 mM sodium pyruvate (American International Chemical Inc., Natick, Mass.) or 10 mM L-carnitine in combination with 10 mM sodium pyruvate. At the end of a 3-hour incubation period, alamarBlue™ was added to each well and the plates returned to the incubator. After 1 hour the fluorescence was measured using a CytoFluor® Fluorescence Plate Reader (PerSeptive Biosystems, Framingham, Mass.) set with the following filter-combination: excitation at 530 nm and emission at 590 nm.

We found that when NHDF were exposed to medium containing mineral water and sodium pyruvate or mineral water and carnitine, it resulted in only a minor increase in metabolic activity, i.e., the mineral water and sodium pyruvate increased metabolic activity by 2.16% (n=8) while the mineral water and carntine increased metabolic activity by 6.05% (n=8). However, when NHDF were exposed to a cocktail of mineral water, sodium pyruvate and canitine, an unexpected enhancement of skin cell metabolism was observed, resulting in an increase of 25.82% (n=8). Thus, in the presence of this cocktail, the energy production was significantly greater than the sum of the individual components.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of promoting metabolism in skin cells, said method comprising topically administering a promoting amount of (i) carnitine or a therapeutically acceptable salt or ester thereof and (ii) pyruvic acid or a therapeutically acceptable salt or ester thereof.

2. A method of promoting energy production in skin cells, said method comprising topically administering a promoting amount of (i) carnitine or a therapeutically acceptable salt or ester thereof and (ii) pyruvic acid or a therapeutically acceptable salt or ester thereof.

3. A method of promoting the uptake of oxygen into the skin, said method comprising topically administering a promoting amount of (i) carnitine or a therapeutically acceptable salt or ester thereof and (ii) pyruvic acid or a therapeutically acceptable salt or ester thereof.

4. A method of promoting the utilization of oxygen by skin cells, said method comprising topically administering a promoting amount of (i) carnitine or a therapeutically acceptable salt or ester thereof and (ii) pyruvic acid or a therapeutically acceptable salt or ester thereof.

5. A method of claim 1, wherein said method further comprises topically administering mineral water having a mineralization of at least about 200 mg/L, wherein said mineral water comprises at least about 10 mg/L of calcium and at least about 5 mg/L of magnesium.

6. A method of claim 2, wherein said method further comprises topically administering mineral water having a mineralization of at least about 200 mg/L, wherein said mineral water comprises at least about 10 mg/L of calcium and at least about 5 mg/L of magnesium.

7. A method of claim 3, wherein said method further comprises topically administering mineral water having a mineralization of at least about 200 mg/L, wherein said mineral water comprises at least about 10 mg/L of calcium and at least about 5 mg/L of magnesium.

8. A method of claim 4, wherein said method further comprises topically administering mineral water having a mineralization of at least about 200 mg/L, wherein said mineral water comprises at least about 10 mg/L of calcium and at least about 5 mg/L of magnesium.

9. A method of claim 5, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) from about 0.1 mg/L to about 5 mg/L of potassium.

10. A method of claim 9, wherein said mineral water further comprises (e) from about 1 to about 20 mg/L of sulphates; (f) from about 1 to about 10 mg/L of sodium; (g) from about 1 mg/L to about 10 mg/L of chlorides; and (h) from about 1 mg/L to about 10 mg/L of nitrates.

11. A method of claim 6, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) from about 0.1 mg/L to about 5 mg/L of potassium.

12. A method of claim 11, wherein said mineral water further comprises (e) from about 1 to about 20 mg/L of sulphates; (f) from about 1 to about 10 mg/L of sodium; (g) from about 1 mg/L to about 10 mg/L of chlorides; and (h) from about 1 mg/L to about 10 mg/L of nitrates.

13. A method of claim 7, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) from about 0.1 mg/L to about 5 mg/L of potassium.

14. A method of claim 13, wherein said mineral water further comprises (e) from about 1 to about 20 mg/L of sulphates; (f) from about 1 to about 10 mg/L of sodium; (g) from about 1 mg/L to about 10 mg/L of chlorides; and (h) from about 1 mg/L to about 10 mg/L of nitrates.

15. A method of claim 8, wherein said mineral water comprises (a) from about 30 mg/L to about 150 mg/L of calcium; (b) from about 10 mg/L to about 50 mg/L of magnesium; (c) from about 150 mg/L to about 700 mg/L of bicarbonates; and (d) from about 0.1 mg/L to about 5 mg/L of potassium.

16. A method of claim 15, wherein said mineral water further comprises (e) from about 1 to about 20 mg/L of sulphates; (f) from about 1 to about 10 mg/L of sodium; (g) from about 1 mg/L to about 10 mg/L of chlorides; and (h) from about 1 mg/L to about 10 mg/L of nitrates.

17. A method of claim 5, wherein said mineral water is from Evian, France.

18. A method of claim 6, wherein said mineral water is from Evian, France.

19. A method of claim 7, wherein said mineral water is from Evian, France.

20. A method of claim 8, wherein said mineral water is from Evian, France.

21. A method of claim 1, wherein said method comprises topically administering a lip balm, skin cleansing composition, shampoo, moisturizing lotion, moisturizing cream, sunscreen lotion, or sunscreen cream comprising such promoting amount of (i) carnitine or a therapeutically acceptable salt or ester thereof and (ii) pyruvic acid or a therapeutically acceptable salt or ester thereof.

22. A method of claim 2, wherein said method comprises topically administering a lip balm, skin cleansing composition, shampoo, moisturizing lotion, moisturizing cream, sunscreen lotion, or sunscreen cream comprising such promoting amount of (i) carnitine or a therapeutically acceptable salt or ester thereof and (ii) pyruvic acid or a therapeutically acceptable salt or ester thereof.

23. A method of claim 3, wherein said method comprises topically administering a lip balm, skin cleansing composition, shampoo, moisturizing lotion, moisturizing cream, sunscreen lotion, or sunscreen cream comprising such promoting amount of (i) carnitine or a therapeutically acceptable salt or ester thereof and (ii) pyruvic acid or a therapeutically acceptable salt or ester thereof.

24. A method of claim 4, wherein said method comprises topically administering a lip balm, skin cleansing composition, shampoo, moisturizing lotion, moisturizing cream, sunscreen lotion, or sunscreen cream comprising such promoting amount of (i) carnitine or a therapeutically acceptable salt or ester thereof and (ii) pyruvic acid or a therapeutically acceptable salt or ester thereof.

25. A method of claim 17, wherein said method comprises topically administering a lip balm, skin cleansing composition, shampoo, moisturizing lotion, moisturizing cream, sunscreen lotion, or sunscreen cream comprising such mineral water and such promoting amount of (i) carnitine or a therapeutically acceptable salt or ester thereof and (ii) pyruvic acid or a therapeutically acceptable salt or ester thereof.

26. A method of claim 18, wherein said method comprises topically administering a lip balm, skin cleansing composition, shampoo, moisturizing lotion, moisturizing cream, sunscreen lotion, or sunscreen cream comprising such mineral water and such promoting amount of (i) carnitine or a therapeutically acceptable salt or ester thereof and (ii) pyruvic acid or a therapeutically acceptable salt or ester thereof.

27. A method of claim 19, wherein said method comprises topically administering a lip balm, skin cleansing composition, shampoo, moisturizing lotion, moisturizing cream, sunscreen lotion, or sunscreen cream comprising such mineral water and such promoting amount of (i) carnitine or a therapeutically acceptable salt or ester thereof and (ii) pyruvic acid or a therapeutically acceptable salt or ester thereof.

28. A method of claim 20, wherein said method comprises topically administering a lip balm, skin cleansing composition, shampoo, moisturizing lotion, moisturizing cream, sunscreen lotion, or sunscreen cream comprising such mineral water and such promoting amount of (i) carnitine or a therapeutically acceptable salt or ester thereof and (ii) pyruvic acid or a therapeutically acceptable salt or ester thereof.

\* \* \* \* \*